(12) United States Patent
Schlogl et al.

(10) Patent No.: US 7,790,650 B2
(45) Date of Patent: Sep. 7, 2010

(54) CATALYST COMPRISING NANOCARBON STRUCTURES FOR THE PRODUCTION OF UNSATURATED HYDROCARBONS

(75) Inventors: Robert Schlogl, Berlin (DE); Gerhard Mestl, München (DE)

(73) Assignee: NanoC Sdn. Bhd., Kuala Lumpur (MY)

( * ) Notice: Subject to any disclaimer, the term of this patent is extended or adjusted under 35 U.S.C. 154(b) by 903 days.

(21) Appl. No.: 11/632,513

(22) PCT Filed: Jul. 13, 2005

(86) PCT No.: PCT/EP2005/007619

§ 371 (c)(1),
(2), (4) Date: Jan. 16, 2007

(87) PCT Pub. No.: WO2006/008049

PCT Pub. Date: Jan. 26, 2006

(65) Prior Publication Data

US 2008/0071124 A1    Mar. 20, 2008

(30) Foreign Application Priority Data

Jul. 16, 2004    (DE) ...................... 10 2004 034 630

(51) Int. Cl.
*B01J 27/224*  (2006.01)
*B01J 21/18*   (2006.01)
*B01J 23/00*   (2006.01)
*B01J 21/00*   (2006.01)
*B01J 23/02*   (2006.01)
*B01J 23/06*   (2006.01)
*C07C 5/09*    (2006.01)
*C07C 15/40*   (2006.01)
*C07C 4/02*    (2006.01)
*C07C 5/00*    (2006.01)
*C07C 2/00*    (2006.01)
*C07C 5/327*   (2006.01)
*C07C 5/373*   (2006.01)

(52) U.S. Cl. ........................ 502/178; 502/180; 502/182; 502/184; 502/242; 502/243; 502/246; 502/251; 502/340; 502/341; 502/350; 502/355; 585/435; 585/440; 585/500; 585/616; 585/654; 977/740; 977/741; 977/744; 977/745; 977/748

(58) Field of Classification Search .................. 502/178, 502/180, 182, 184, 242, 243, 246, 251, 340, 502/341, 350, 351, 355; 585/435, 440, 500, 585/616, 654; 977/740, 741, 744, 745, 748
See application file for complete search history.

(56) References Cited

U.S. PATENT DOCUMENTS 6,017,390 A    1/2000    Charych et al.

7,399,703 B2 *  7/2008   Kawakami ................... 438/669
2003/0124717 A1  7/2003   Awano et al.
2009/0220767 A1 * 9/2009  Schlogl et al. .............. 428/323

FOREIGN PATENT DOCUMENTS

WO    WO2004035882    4/2004

OTHER PUBLICATIONS

"Catalytic activity of carbon nanotubes and other carbon materials for oxidative dehydrogenation of ethylbenzene to styrene," N. Maksimova et al. Studies in Surface Science and Catalysis 133 (2001), pp. 383-389.*
"Nanocarbons in selective oxidative dehydrogenation reaction," D. S. Su et al. Catalysis Today 102-103 (2005), pp. 110-114.*
"Catalytic synthesis of carbon nanostructures from polymer precursors," Nadezhda I. Maksimova et al. Journal of Molecular Catalysis A: Chemical 158 (2000), pp. 301-307.*
"Large scale synthesis of carbon nanofibers by catalytic decomposition of ethane on nickel nanoclusters decorating carbon nanotubes," Cuong Pham-Huu et al. Phys. Chem. Chem. Phys., 2002, 4, pp. 514-521.*
"Rational Design of the carbon nanofiber catalysts for oxidative dehydrogenation of ethylbenzene," Tie-Jun Zhao et al. Applied Catalysis A: General 323 (2007), pp. 135-146.*
"Influence of the microstructure of carbon nanotubes on the oxidative dehydrogenation of ethylbenzene to styrene," J. J. Delgado et al. Catalysis Today 150 (2010), pp. 49-54.*
F, Cavani, et al. Alternative processes for the production of styrene, Applied Catalysts, 1995 Elsevier Science B.V., pp. 221-239.
Wang, S. et al., "Studies on the Preparation of Alumina Supported on Carbon Nanotubes and Defluorination from Absorbed Water", Academic Chemical Journal, 2003, pp. 95-99, 24 (1), together with English-language abstract.
Keller, N., et al., "The Catalytic Use of Onion-Like Carbon Materials for Styrene Synthesis by Oxidative Dehydrogenation of Ethylbenzene", Angewandte Chemie International Edition, May 28, 2002, pp. 1885-1888, vol. 41, Issue 11.

* cited by examiner

*Primary Examiner*—Patricia L Hailey
(74) *Attorney, Agent, or Firm*—Scully, Scott, Murphy & Presser, P.C.

(57) ABSTRACT

The present invention relates to catalysts comprising at least one support and at least one layer applied to said support, said layer containing a) 20 to 95% by weight of at least one aluminum, silicon, titanium or magnesium oxide compound or a silicon carbide or a carbon support or mixtures thereof, and b) 5 to 50% by weight of at least one nanocarbon. The catalysts can be used to produce unsaturated hydrocarbons by means of the oxidative dehydrogenation of alkylaromatics, alkenes and alkanes in the gas phase.

12 Claims, No Drawings

CATALYST COMPRISING NANOCARBON STRUCTURES FOR THE PRODUCTION OF UNSATURATED HYDROCARBONS

The invention relates to catalysts for the production of unsaturated or polyunsaturated hydrocarbons from alkylaromatics, alkenes or alkanes by means of oxidative dehydrogenation in the gas phase, as well as to a method for the production of unsaturated hydrocarbons using such catalysts.

In the oxidative dehydrogenation of hydrocarbons, in particular unsaturated hydrocarbons, in the gas phase, alkylaromatics, alkenes or alkanes or mixtures of alkylaromatics, alkenes or alkanes with air or with other oxygen-containing gases are passed over a catalyst. The catalyst is thereby normally placed in the tubes of a tube-bundle reactor, however the catalyst can alternatively also be placed in a fluidised bed of a fluidised bed reactor. Heating to the required reaction temperature and cooling of exothermic reactions is carried out using a salt melt which surrounds the tubes or the fluidised bed reactor. The reactor can alternatively also be brought to the necessary reaction temperature by means of electric resistance heating or another common heating.

The prior art thus relates to the endothermic, direct dehydrogenation of alkylaromatics, alkenes or alkanes, for example over potassium-promoted iron oxide catalysts. In order to improve selectivity and/or yield, activating or even activity-lowering additives, for example oxides of elements of the subgroup of the periodic table of the elements or alkali compounds, are often also added in small amounts as dopants (promoters). It is known from RU 2187364, for example, that iron oxide catalysts are promoted with $K_2O$, MgO, $MoO_3$, $Ce_2O_3$, $Sr_2O$ and $La_2O_3$. It is common in the cited prior art that the production of unsaturated hydrocarbons is carried out by means of direct dehydrogenation over oxide-containing catalysts.

The object of the invention was to provide catalysts for the production of monounsaturated, diunsaturated and polyunsaturated hydrocarbons by means of the oxidative dehydrogenation, for example, of alkylaromatics, alkenes or alkanes in the gas phase. In comparison to conventional oxidic catalysts for direct dehydrogenation, these catalysts are supposed to catalyse exothermic oxidative dehydrogenation with increased yields.

The subject matter of the invention is catalysts, in particular supported catalysts, for the production of monounsaturated, diunsaturated and polyunsaturated hydrocarbons by means of the oxidative dehydrogenation, for example, of allkylaromatics, alkenes and/or alkanes in the gas phase. These catalysts comprise a support and a layer applied thereto.

Disclosed in particular are catalysts according to the invention that comprise at least one support and at least one layer provided on the support, said layer
a) containing 50 to 95% by weight of at least one aluminium, silicon, titanium or magnesium oxide compound or a silicon carbide or a carbon support or mixtures of at least two of the above compounds, and
b) 5 to 50% by weight of at least one nanocarbon material.

The aluminium, silicon, titanium and magnesium oxide compounds are thereby preferably calculated as oxide and the silicon carbide as carbide.

The support, which is preferably inert, can have any shape and surface structure. However, regularly shaped, mechanically stable bodies such as spheres, rings, tube sections, half-rings, saddles, spirals or honeycomb support bodies or support bodies provided with channels such as, for example, fibre mats or ceramic foams are preferred. The size and shape of the support bodies is determined, for example, by the dimensions, primarily the internal diameter of the reaction tubes if the catalyst is used in tube or tube-bundle reactors. The diameter of the support body should then be between ½ and ⅒ of the internal diameter of the reactor. In the case of fluidised bed reactors, the support dimensions are determined, for example, by the fluid dynamics in the reactor. Suitable materials are, for example, steatite, duranite, stoneware, porcelain, silicon dioxide, silicates, aluminium oxide, aluminates, silicon carbide or mixtures of these substances. Tube sections, rings or spheres made of ceramic, silicon carbide or carbon are preferably used.

The proportion of the layer applied to the support is preferably 1 to 30% by weight, particularly preferred 2 to 20% by weight, based on the total mass of the catalyst. The thickness of the layer is preferably 5 to 300 μm, particularly preferred 5 to 10 μm.

A compound having a specific surface area of 1 to 50 $m^2/g$ is preferably used as component a). Silicon carbide or titanium oxide, for example, is preferably used, with it being particularly preferred for them to have a specific surface area of 1 to 50 $m^2/g$. Aluminium oxide in the gamma modification with a BET surface area of 50 to 100 $m^2/g$, magnesium oxide with a surface area of 10 to 50 $m^2/g$ or a carbon support, e.g. active carbon, with a surface area of 1 to 5 $m^2/g$ is preferably alternatively or additionally used. A proportion of 70 to 95% by weight of component a), based on the total weight of the layer, is preferably used.

In a preferred embodiment, the supports are coated with an aqueous slurry or a suspension in an organic solvent such as, for example, toluene, of component a) and a nanocarbon material b) as well as, optionally, a binder, and are dried, for example, in a rotary tube furnace at, for instance, 200 to 300° C. The aqueous or organic slurry or suspension of component a) and the nanocarbon material b) can, however, also be applied separately yet in one layer, for example, by first applying a layer of the support from a slurry, drying at 200 to 300° C. and then subsequently depositing the nanocarbon catalyst from the slurry or organic suspension into the pores of the support. The support catalyst is then dried a further time at 200 to 300° C.

The nanocarbon according to the invention preferably comprises or preferably consists of carbon rings in which one, two or several ring carbon atoms have optionally been replaced by heteroatoms such as oxygen or nitrogen. The carbon rings can thereby comprise 6, for example, 5 ring atoms. It is particularly preferred for the nanocarbons to be selected from nanocarbon tubes, nanocarbon filaments, nanocarbon onions and nanographite or mixtures thereof. Nanocarbon tubes, nanocarbon filaments and nanographite are described, for example, in the following citations: CARBON NANOFILAMENTE IN DER HETEROGENEN KATALYSE: EINE TECHNISCHE ANWENDUNG FÜR KOHLENSTOFFMATERIALIEN?, G. Mestl, N. I. Maximova, N. Keller. V. V. Roddatis and R. Schlögl, Angew. Chem., 113, 2122-2125 (2001): "CATALYTIC ACTIVITY OF CARBON NANOTUBES AND OTHER CARBON MATERIALS FOR OXIDATIVE DEHYDROGENATION OF ETHYLBENZENE TO STYRENE", N. Maksimova, G. Mestl and R. Schlögl, in Reaction Kinetics and the Development and Operation of Catalytic Processes, Studies in Surface Science and Catalysis, Vol 133, pages 383-390, 2001; "OXIDATIVE DEHYDROGENATION OF ETHYLBENZENE TO STYRENE OVER CARBONACEOUS MATERIALS", N. I. Maximova, V. V. Roddatis, G. Mestl, M. Ledoux and R. Schlögl, Eurasian Chem. Tech. J., 2, 231-236 (2000), and nanocarbon onions are described in the following citations: "THE FIRST CATALYTIC USE OF ONION-LIKE CARBON MATERIALS: THE STYRENE SYNTHESIS", N. Keller, N. I. Maksimova, V. V. Roddatis, M. Schur, G.

Mestl, Y. V. Butenko, V. L. Kuznetsov and R. Schlögl, Angew. Chem., 114, 1962-1966 (2002). The entire content of these citations is included in the present application.

The nanocarbon tubes and/or nanocarbon filaments can preferably comprise walls which are orientated either parallel to the tube or filament axis or perpendicular to the tube or filament axis or which form, with the tube or filament axis, an angle of >0° to <90°. Nanocarbons normally consist exclusively of carbon, however up to 5% of the surface atoms of nanocarbons can consist of heteroatoms such as oxygen or nitrogen. Nanotubes or filaments have a diameter of 1 to 50 nm and lengths of 10 to several hundred nm. They can be produced in a manner known per se. How such materials can be produced is described, for example, in "LARGE SCALE SYNTHESIS OF CARBON NANOFIBERS BY CATALYTIC DECOMPOSITION OF ETHANE ON NICKEL NANOCLUSTERS DECORATING CARBON NANOTUBES", C. Pham.Huu, N. Keller, V. Roddatis, G. Mestl, R. Schlögl and M. Ledoux, PCCP, 4, 514-521 (2002) and "CATALYTIC SYNTHESIS OF CARBON NANOSTRUCTURES FROM POLYMER PRECURSORS", N. Maximova, O. P. Krivoruclhko, G. Mestl, V. I. Zaikovskii, A. L. Chuvilin, A. N. Salanov and E. B. Burgina, J. Mol. Catal. A, 158, 301-307 (2000). The entire content of these citations is included in the present application.

The supported nanocarbon catalysts can furthermore be doped with other elements, whereby the selectivity and activity can be increased or if necessary, the activity can alternatively be lowered. The nanocarbons can be doped for this purpose with further elements of the PSE (Periodic Table of the Elements) before and/or after supporting, and in the second case, the supported catalyst should be heat-treated a further time. Elements of the subgroup of the PSE or O, N, P, S, Sb, Bi, preferably as water-soluble salts or salts that are soluble in an organic solvent are preferably used as dopants (promoters). The nanocarbon supported catalyst according to the invention can therefore be further improved as regards its activity and selectivity, for example, by means of impregnation with a maximum of 1% by weight of potassium nitrate or a maximum of 1% by weight of vanadium oxalate from an aqueous solution.

The nanocarbon supported catalysts can, however, also be customised as regards their activity and/or selectivity by means of a suitable oxidative treatment, in particular a pretreatment, wherein, for example, treatment in air or oxygen-containing gases at temperatures of preferably 300 to 700° C., or a treatment in oxidising liquids such as, for example, nitric acid-containing liquids or hydrogen peroxide is carried out. The nanocarbon can be hereby doped with oxygen and/or nitrogen atoms on the surface and the catalytic properties thereof can be modified.

Supported catalysts with well adhering coatings, which is important in particular for the transport and filling of the catalyst in the reactor, can be obtained, for example, by applying to the support, as mentioned above, an aqueous or organic slurry or suspension containing the mixture or the individual components for the layer to be applied as well as, optionally, an organic binder. The layer is advantageously applied evenly.

In an alternative manner, it is possible to produce the supported catalyst initially without component b), i.e. the nanocarbon, whereby it is impregnated with a small amount (for example 1 to 10% by weight, preferably 4 to 6% by weight and particularly preferred approximately 5% by weight) of iron. The iron can thereby be present in a common form, preferably as a fine powder.

When the reactor into which the supported catalyst has been inserted is started up, a flow of the material to be reacted, e.g. ethylbenzene, can be introduced, preferably under the exclusion of oxygen, whereby the nanocarbon, component b, forms on the supported catalyst. After the start up period, the oxygen-containing gas is also introduced in the reactor.

Preferred as organic binders are copolymers, preferably in the form of an aqueous dispersion of vinyl acetate/vinyl laurate, vinyl acetate/acrylate, styrene/acrylate, vinyl acetate/maleate as well as vinyl acetate/ethylene. Amounts of the binder of 2 to 5% by weight, based on the solids content of the suspension, are normally completely sufficient. These copolymers are completely combusted within a short amount of time in the airflow after drying or during starting of the reactor.

The nanocarbon supported catalysts are suitable for use as catalysts in oxidative dehydrogenation for the production of unsaturated hydrocarbons such as, for example, styrene from ethylbenzene, butadiene from butylene and butylene and/or butadiene from butane in the gas phase.

The hydrocarbons to be produced are, for example, substituted unsaturated aromatic hydrocarbons, i.e. aromatic hydrocarbons such as benzene, naphtheline or anthrazene, which can comprise one or more substituents.

Examples of substituents are unsaturated hydrocarbons having 2 to 10, preferably 3 to 6 carbon atoms, the substituents containing one, two or several double and/or triple bonds.

According to a further embodiment, the hydrocarbons to be produced are monounsaturated or polyunsaturated aliphatic hydrocarbons, i.e. olefinic hydrocarbons having 3 to 20, preferably 4 to 6, carbon atoms and one, two or several double and/or triple bonds.

The unsaturated aliphatic hydrocarbons preferably comprise at least two double and/or triple bonds.

Alkanes having 3 to 20, preferably 3 or 4-6 carbon atoms, can be used as starting products, which can be unsubstituted or can have one or more substituents, the substituents being defined as specified above.

Unsaturated hydrocarbons, as defined above (i.e., for example, optionally substituted unsaturated or substituted unsaturated aromatic hydrocarbons), can furthermore be used as starting products and have at least one multiple bond less than the hydrocarbon to be produced. If the hydrocarbon to be produced is supposed to have, for example, two multiple bonds, an unsaturated hydrocarbon having one or no multiple bonds is used, and if the hydrocarbon to be produced is supposed to have, for example, three multiple bonds, an unsaturated hydrocarbon having one or two multiple bonds is used.

In an alternative manner, the starting product can also have one or more double bonds, which are converted into one or more triple bonds according to the invention.

In order to produce unsaturated hydrocarbons, the respective starting materials are introduced preferably into fixed-bed or fluidised bed reactors together with oxygen-containing gases in the presence of the catalyst according to the invention. Typical fixed-bed reactors are, for example, reaction tubes which are collected into tube-bundle reactors and are surrounded by a heat exchange medium. The reactors can alternatively also be heated by means of electric resistance heating or firing to the necessary reaction temperature. The reaction tubes are preferably arranged vertically and the reaction mixture flows through them from the top, alternatively from the bottom. They preferably comprise a material that is inert towards the heat exchange medium, the catalyst, the starting materials and the products, generally steel, and have a length, for example, of 1000 to 10,000 mm, an internal diameter, for example, of 10 to 30 mm and a wall thickness, for example, of 1 to 4 mm.

Eutectic salt mixtures, such as, for example, a chloride-fee melt of potassium nitrate, sodium nitrate and sodium nitrite have proven themselves suitable as heat exchange media in practice. The temperature of the salt melt, which essentially has the object of removing the heat quantity released during the exothermic reaction, is generally 300° C. to 500° C.

The nanocarbon catalyst is preferably introduced into the reaction tubes or the fluidised bed reactor from the top. In the case of the fixed-bed reactor, the catalyst is preferably fixed by holders disposed in the vicinity of the lower ends of the tubes. The filling height can be, for example, 500 to 9500 mm. The reaction tubes can be optionally filled in layers with support bodies of different shapes and sizes as well as different concentrations and compositions of the active components.

The reaction gas, which contains, for example, starting hydrocarbons and an oxygen-containing gas, preferably air, is passed over the catalysts at a space velocity of, for example, 0.1 to 10,000 $h^{-1}$, preferably 1 to 6000 $h^{-1}$. The mixture of process air and hydrocarbon, which passes over the catalyst disposed in the reaction tubes from top to bottom, or alternatively from bottom to top, is normally preheated to 100° C. to 300° C. The mixing ratio is thereby 10 to 200 g of hydrocarbon per standard cubic meter of oxygen-containing gas. 2 to 40% of water vapour can be optionally added to the process gas. Following the reaction, the product formed is isolated from the reaction gas in a manner known per se by distillation, freezing out, or by corresponding gas-washing with a suitable solvent.

The nanocarbon supported catalysts according to the invention are distinguished from the hitherto dehydrogenation catalysts in that the reaction can be carried out as exothermic oxidative dehydrogenation that generates energy and can thus be carried out with a considerably lower expenditure of energy as compared to the prior art. The nanocarbon supported catalysts according to the invention are furthermore distinguished from the prior art in that the reaction can be carried out without the addition of superheated water vapour, which also contributes to a clear saving of energy. The nanocarbon catalysts according to the invention are thus characterised by high selectivities of up to 95% for the respectively desired product, and starting product conversions of up to 70%.

The following examples are used to further explain the invention.

Catalyst Preparation

The catalyst components were suspended in the amounts specified in table 1, for example, in 100 ml to 1000 ml of deionised water and were stirred for 1 to 18 hours in order to obtain homogeneous dispersion. Before the mixture was applied to the steatite support body specified in table 1, 10 to 50 g of organic binder, a copolymer of vinyl acetate and vinyl laurate in the form of a 50% aqueous dispersion, were added to the suspension. The aqueous suspension was then sprayed onto the support in a fluidised bed. Heating of the catalyst occurred directly in the reactor at 380° C. to 450° C. for 24 to 32 hours.

The composition of the catalysts according to the invention (A to D) and that of the comparison catalysts (E, conventional composition) is given in table 1.

TABLE 1

| A | B | C | D | E |
|---|---|---|---|---|
| Steatite spheres Ø 1 mm | Steatite spheres Ø 1 mm | Steatite spheres Ø 1 mm | Steatite spheres Ø 1 mm | Steatite spheres Ø 1 mm |
| 90% by weight $TiO_2$ | 90% by weight $TiO_2$ | 90% by weight $TiO_2$ | 90% by weight $TiO_2$ | 60% by weight $FE_2O_3$ |
| 10% by weight nanocarbon tubes | 10% by weight nanocarbon filaments | 10% by weight nanocarbon onions | 10% by weight nanographite | 16% by weight $K_2O$ |

Dehydrogenation

The oxidative dehydrogenation tests were carried out in a reaction tube designed for use on an industrial scale. The length of the reaction tube was 1.2 m (filling height 70 cm), and the diameter thereof was 26 mm. The temperature of the reactor was controlled using a circulated salt bath (eutectic, chloride-free melt of potassium nitrate, sodium nitrate and sodium nitrite). 60 g of each supported catalyst was placed in the reactor. The reaction temperature is specified in table 2 with the letter T. The amount of oxygen-containing gas fed into the reactor was 60 $Nm^3/h$; the abbreviation EB in the table refers to the adjusted amount of ethylbenzyne in oxygen-containing gas in g of ethylbenzene per $Nm^3/h$ gas. The space-time velocity was 1 $l/g^{-1}h^{-1}$ in all of the experiments. The pure yields of styrene A of the nanocarbon catalysts of the invention as compared to conventional catalysts are given in table 2.

TABLE 2

|  | A | B | C | D | E* |
|---|---|---|---|---|---|
| T [° C.] | 450 | 450 | 450 | 450 | 680 |
| EB [g/$Nm^3$/h] | 15 | 15 | 15 | 15 | 15 |
| A [%] | 81 | 75 | 89 | 70 | 60 |

*measured under normal dehydrogenation conditions.

The comparison catalyst E corresponds to a conventional potassium-promoted iron catalyst. The comparison with the catalysts according to the invention shows that in comparison to potassium-promoted iron catalysts, catalysts having the nanocarbons according to the invention cause a clear lowering of the reactor temperature as well as a clear increase in yield in the oxidative dehydrogenation of ethylbenzene.

The invention claimed is:

1. A catalyst comprising at least one support and at least one layer applied as coating to said support, said layer containing
    a) 50 to 95% by weight of at least one aluminum, silicon, titanium or magnesium oxide compound or a silicon carbide or a carbon support or mixtures thereof, and
    b) 5 to 50% by weight of at least one nanocarbon.

2. A catalyst according to claim 1, wherein the support is an inert support.

3. A catalyst according to claim 1, wherein the nanocarbon contains at least one carbon ring, in which one or more ring carbon atoms are optionally replaced with heteroatoms such as oxygen or nitrogen.

4. A catalyst according to claim 3, wherein the carbon rings comprise 6 ring atoms.

5. A catalyst according to claim 1, wherein the nanocarbon is selected form nanocarbon tubes, nanocarbon filaments, nanocarbon onions and nanographite or mixtures thereof.

6. A catalyst according to claim 5, wherein the nanocarbon tubes and/or nanocarbon filaments have walls that are oriented either parallel to the tube axis or perpendicular to the tube axis or which form an angle of >0° to <90° with the tube axis.

7. A catalyst according to claim 1, characterised in that it additionally comprises at least one promoter.

8. A catalyst according to claim 7, characterised in that the at least one promoter is selected from a subgroup of the periodic table of the elements or from an alkali metal.

9. A catalyst according to claim 7, characterised in that the at least one promoter is selected from O, S, N, P, Sb and Bi and is preferably formulated as a water-soluble salt or a salt that is soluble in an organic solvent.

10. Method for the production of optionally substituted unsaturated aromatic hydrocarbons, characterised in that alkylaromatics are reacted in the gas phase in the presence of a catalyst according to claim 1 by catalytic oxidative dehydrogenation.

11. Method for the production of polyunsaturated aliphatic hydrocarbons, characterised in that alkenes are reacted in the gas phase in the presence of a catalyst according to claim 1 by catalytic oxidative dehydrogenation.

12. Method for the production of monounsaturated aliphatic hydrocarbons, characterised in that alkanes are reacted in the gas phase in the presence of a catalyst according to claim 1 by catalytic oxidative dehydrogenation.

* * * * *